United States Patent

Sauer et al.

[11] Patent Number: 5,219,862
[45] Date of Patent: Jun. 15, 1993

[54] 8BETA-SUBSTITUTED ERGOLINES, PROCESS FOR THEIR PRODUCTION AND THEIR USE

[75] Inventors: Gerhard Sauer; Thomas Brumby; Helmut Wachtel; Jonathan Turner; Peter A. Loschmann, all of Berlin, Fed. Rep. of Germany

[73] Assignee: Schering Aktiengesellschaft, Berlin and Bergkamen, Fed. Rep. of Germany

[21] Appl. No.: 623,933
[22] PCT Filed: Apr. 6, 1990
[86] PCT No.: PCT/DE90/00282
  § 371 Date: Dec. 21, 1990
  § 102(e) Date: Dec. 21, 1990
[87] PCT Pub. No.: WO90/12796
  PCT Pub. Date: Nov. 1, 1990

[30] Foreign Application Priority Data

Apr. 21, 1989 [DE] Fed. Rep. of Germany ....... 3913756

[51] Int. Cl.$^5$ ............ C07D 457/06; C07D 457/02; A61K 31/48
[52] U.S. Cl. .................... 514/288; 544/125; 546/67; 546/69
[58] Field of Search ............ 544/125; 546/67, 69; 514/288

[56] References Cited

U.S. PATENT DOCUMENTS

| | | | |
|---|---|---|---|
| 4,054,660 | 10/1977 | Clemens et al. | 546/67 |
| 4,246,285 | 1/1981 | Kornfeld et al. | 546/67 |
| 4,321,380 | 3/1982 | Cerny et al. | 546/67 |
| 4,847,262 | 5/1989 | Sauer et al. | 546/67 |

FOREIGN PATENT DOCUMENTS

| | | | |
|---|---|---|---|
| 3667 | 8/1979 | European Pat. Off. | 546/67 |
| 3150918 | 4/1983 | Fed. Rep. of Germany | 546/67 |
| 657366 | 8/1986 | Switzerland | 546/67 |
| 2074566 | 4/1980 | United Kingdom | 546/67 |
| 2103603 | 8/1981 | United Kingdom | 546/67 |
| 2125041 | 4/1984 | United Kingdom | 546/67 |

OTHER PUBLICATIONS

Krepelka, et al. Chem. Abstracts, vol. 88, 1978 Abstract 121501q.
Krepelka, et al. Chem. Abstracts, vol. 96, 1982 Abstract 181490k.
Grant and Hackh's Chemical Dictionary (McGraw-Hill Books, New York, 1987) p. 14

Primary Examiner—Robert T. Bond
Assistant Examiner—E. C. Ward
Attorney, Agent, or Firm—Millen, White, Zelano & Branigan

[57] ABSTRACT

Compounds of formula I

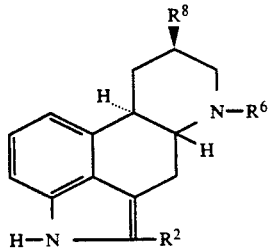

in which
R$^2$ means optionally substituted C$_{1-7}$ alkyl, C$_{2-7}$ alkenyl, CH$_2$—O—C$_{1-4}$ alkyl or CH$_2$—S—C$_{1-4}$ alkyl
R$^6$ means C$_{2-6}$ alkyl, C$_{3-6}$ alkenyl or C$_{3-5}$-cycloalkyl-C$_{1-2}$ alkyl and
R$^8$ means CH$_2$—X,

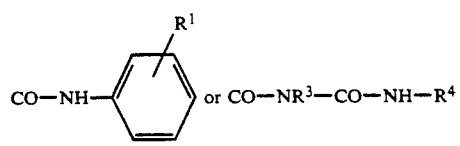

in which
X stands for CN, OCH$_3$, SCH$_3$ or CONH$_2$ and R$^1$ stands for hydrogen, halogen, methyl or methoxy, and R$^3$ and R$^4$ each mean C$_{1-4}$ alkyl or (CH$_2$)$_n$—N(CH$_3$)$_2$, in which n=1-4, and their acid addition salts, the process for their production, their use as pharmaceutical agents as well as intermediate compounds are described.

5 Claims, No Drawings

8BETA-SUBSTITUTED ERGOLINES, PROCESS FOR THEIR PRODUCTION AND THEIR USE

The invention relates to ergolines substituted in 2-, 6- and 8beta-positions, their production and their use as pharmaceutical agents.

The ergoline derivatives substituted according to the invention have a long-chain hydrocarbon radical in 6-position, which increases the dopaminergic agonistic activity in comparison with the 6-methyl ergoline derivatives. At the same time, the metabolic stability of the compounds is maintained or is improved.

The invention relates to compounds of the formula I

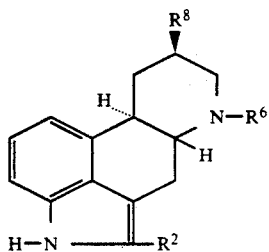

in which
$R^2$ means optionally substituted $C_{1-7}$ alkyl, $C_{2-7}$ alkenyl, $CH_2$—S—$C_{1-4}$ alkyl or $CH_2$—O—$C_{1-4}$ alkyl
$R^6$ means $C_{2-6}$ alkyl, $C_{3-6}$ alkenyl or $C_{3-5}$ cycloalkyl-$C_{1-2}$-alkyl and
$R^8$ means $CH_2$—X,

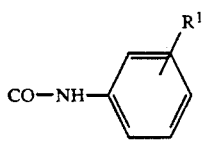

or CO—$NR^3$—CO—$NHR^4$
in which X stands for CN, $OCH_3$, $SCH_3$ or $CONH_2$, $R^1$ stands for hydrogen, halogen, methyl or methoxy, and $R^3$ and $R^4$ each mean $C_{1-4}$ alkyl or $(CH_2)_n$—$N(CH_3)_2$, in which $n = 1-4$ as well as their acid addition salts.

By alkyl is meant a straight-chain or branched alkyl radical such as, for example, methyl, ethyl, n-propyl, isopropyl, n-butyl, isobutyl, sec-butyl, tert-butyl, pentyl, heyxl, heptyl, 2,2-dimethylpropyl, 2-methylbutyl, 3-methylbutyl, 1-ethylbutyl, isopentyl, isoheptyl i.a.

Alkyl radical $R^2$ can be substituted especially in 1-position with a hydroxy, a $C_{1-4}$ alkoxy or a $C_{2-5}$ acyloxy group according to the formula $C(OR')R''R'''$, in which $R''$ and $R'''$ each mean hydrogen or alkyl radicals with a maximum of 6 carbon atoms and $R'$ is especially hydrogen or acetyl.

Aliphatic carboxylic acids such as, for example, acetic acid, propionic acid, butyric acid, caproic acid and trimethylacetic acid i.a. each are suitable as acyl groups.

If $R^2$ or $R^6$ mean an alkenyl radical, the latter preferably contains only one double bond, and the double bond in radical $R^6$ cannot be adjacent to a nitrogen atom. For example, vinyl, 1-propenyl, 2-propenyl, 1-methyl-2-propenyl, 1-butenyl, methallyl are suitable as alkenyl radicals.

If $R^6$ means a cycloalkyl-alkyl group, there is meant, for example, cyclopropylmethyl, cyclopropylethyl, cyclobutylethyl, cyclopentylmethyl, cyclopentylethyl.

The carboxylic acid anilide radical $R^8$ can be substituted singly or doubly in o-, m- or p-position and by halogen is meant fluorine, chlorine, bromine or iodine.

Radicals $R^3$ and $R^4$ are preferably alternating.

Compounds are preferred which have in 2-position an optionally hydroxylated $C_{1-4}$ alkyl or $C_{2-4}$ alkenyl radical or a $CH_2$—O—$CH_3$ or $CH_2$—S—$CH_3$ group. $C_{2-4}$ alkyls, $C_{3-4}$ alkenyls or cycloalkylalkyls with up to 5 carbon atoms are to be considered as preferred embodiment for $R^6$.

The compounds of formula 1 can occur as E or Z isomers or, if a chiral center is present in radical $R^2$, as diastereomers and as their mixtures. The isomers and isomer mixtures are also included in this invention. The physiologically compatible acid addition salts are derived from the known inorganic and organic acids such as, for example, hydrochloric acid, sulfuric acid, hydrobromic acid, citric acid, maleic acid, fumaric acid, tartaric acid, i.a.

The compounds of formula I as well as their acid addition salts especially exhibit centrally dopaminergic effectiveness and are therefore usable as pharmaceutical agents. The dopaminergic agonistic action was determined with the method of the automatic recording of stereotypes on rats described by Horowski (Arzneim. Forsch. 12, 2281-2286, 1978): immediately after intraperitoneal administration of the test substance or vehicle, male Wistar rats (90–120 g) are placed individually in restricted cages of acrylic glass. The number of contacts on a steel bowl with a central metal rod as a result of stereotypical chewing, licking and gnawing movements during 60 minutes is recorded by an electrodynamic recording system applied in front of the head of the animals. Mean values ±SEM of the number of contacts during 60 minutes for the various treatment groups are calculated, and the significance of the differences between the mean values of the various test substance doses in comparison with the vehicle-treated control group is determined with the simple variance analysis in connection with the Dunnett test. The results are shown in Table I:

TABLE I

Triggering of stereotypes in rats during 60 minutes after intraperitoneal treatment with vehicles or with various doses of ergolines (x: p is less than 0.05; xx: p is less than 0.01; variance analysis/ Dunnett test vs. Control), n = number of animals

TABLE I KEY:

Stereotypes [Counts per 60 min.] (mean value ± SEM)

| Verb. η | Kontrolle | 0.025 | 0.1 | 0.39 | 1.56 | 6.25 |
|---|---|---|---|---|---|---|
| A 10 | 1383 ± 139 | 6042 ± 1110 | 8087 ± 1158xx | 9994 ± 797xx | 9085 ± 1318xx | 7258 ± 2250xx |

TABLE I-continued

Triggering of stereotypes in rats during 60 minutes after intraperitoneal treatment with vehicles or with various doses of ergolines (x: p is less than 0.05; xx: p is less than 0.01; variance analysis/ Dunnett test vs. Control), n = number of animals

TABLE I KEY:

Stereotypes [Counts per 60 min.] (mean value ± SEM)

| Verb. $\eta$ | Kontrolle | Test substance dose [mg/kg] | | | | |
|---|---|---|---|---|---|---|
| | | 0.025 | 0.1 | 0.39 | 1.56 | 6.25 |
| B 12 | 911 ± 159 | 3594 ± 985 | 8415 ± 999xx | 10700 ± 750xx | 9126 ± 1022xx | 8337 ± 1237xx |

Verb. = Compound
Kontrolle = Control
A = 8beta-methoxymethyl-2-methyl-6-n-propyl-ergoline
B = (2-methyl-6-n-propyl-8-beta-ergolinyl)-acetonitrile Since they are distinguished especially by a dopaminergic agonistic action, without strong alpha-adrenergic effects occurring, the compounds according to the invention are suitable for treatment of dopamine deficiency conditions in organisms and especially for treatment of Parkinson's disease.

To use the compounds according to the invention as pharmaceutical agents, they are put in the form of a pharmaceutical preparation, which, in addition to the active ingredient for the enteral or parenteral administration, contains suitable pharmaceutical, organic or inorganic inert vehicles such as, for example, water, gelatin, gum arabic, lactose, starch, magnesium stereate, talc, vegetable oils, polyalkylene glycols, etc. The pharmaceutical preparations can be in solid form, for example as tablets, coated tablets, suppositories, capsules, or in liquid form, for example as solutions, suspensions or emulsions. Further, they optionally contain auxiliary agents such as preservatives, stabilizers, wetting agents or emulsifiers, salts to change the osmotic pressure or buffers.

The compounds according to the invention are introduced in a dosage of 0.001 to 10 mg of active substance in a physiologically compatible vehicle. The use of the compounds according to the invention takes place in a dosage of 0.00001 to 0.1 mg/kg/day, preferably 0.001 to 0.1 mg/kg/day analogously to the known agent bromocryptine.

The production of the compounds of formula I according to the invention can be performed according to methods known in the art.

For example, compounds of formula I according to claim 1 are attained by a) a compound of the general formula II

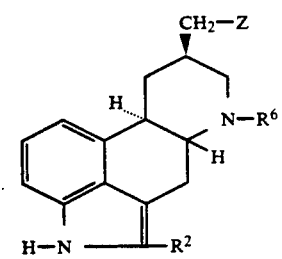

in which $R^2$ and $R^6$ have the above meaning and Z means an easily cleaveable group, being nucleophilically substituted to compounds according to claim 1 with X=CN or SCH$_3$ and, optionally, then the thus obtained acetonitrile derivative being hydrolyzed to the CONH$_2$ group, b) a compound of formula III

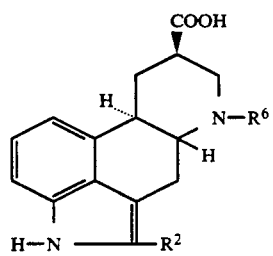

in which $R^2$ and $R^6$ have the above meaning, being reacted with a compound of formula IV

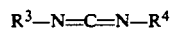

in which $R^3$ and $R^4$ have the above meaning, to compounds according to claim 1 with $R^8$ meaning CO—NR$^3$—CO—NHR$^4$, c) a compound of formula V

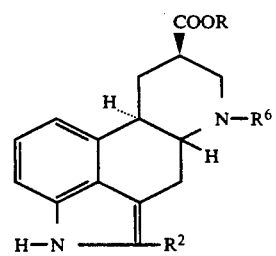

in which $R^2$ and $R^6$ have the above meaning, and R represents a C$_{1-4}$-alkyl group being reacted with an aniline of formula VI

in which $R^1$ has the above meaning, to compounds according to claim 1 with $R^8$ meaning

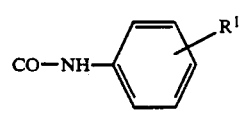

d) a compound of formula VII

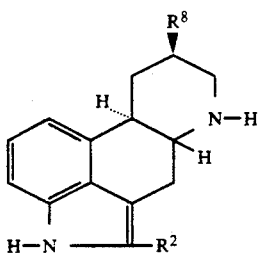

in which $R^2$ and $R^8$ have the above meaning, being alkylated or alkenylated in 6-position, e) a compound of formula VIII

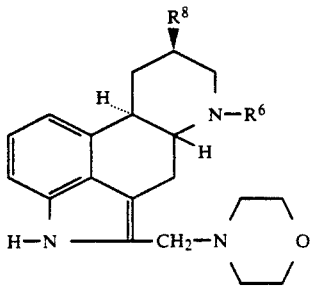

in which $R^6$ and $R^8$ have the above meaning, being converted to a compound according to claim 1 with $R^2$ in the above meaning and, optionally, then forming the acid addition salts.

The reaction of the compounds of formula II according to process a) can, for example, take place according to the process described in EP-A-185 491, by a reactive derivative such as, for example, tosylate, mesylate or iodide reacting at room temperature or at a higher temperature with an alkali salt (such as sodium or potassium salt) of the methyl mercaptide or cyanide in a polar solvent such as dimethylacetamide, dimethylformamide or alcohols.

The optional subsequent conversion of the $CH_2$—CN-group to the $CH_2$—CO—$NH_2$ group takes place according to the usual hydrolysis processes, such as acid treatment, for example with HBr/glacial acetic acid, basic treatment, for example, with sodium hydroxide solution, 30% hydrogen peroxide, tetrabutylammonium hydrogen sulfate in dichloromethane or oxidizing treatment such as $MnO_2$ on silica gel in aqueous acetone, and optionally a suitable inert solvent such as chlorinated hydrocarbons, ethers or aprotic polar solvents can also be added.

The reaction of the compounds of formula III with carbodiimides according to process b) can for example, take place in aprotic solvents such as tetrahydrofuran, dimethylformamide, dichloroethane or dioxane, optionally in the presence of an organic base such as pyridine or triethylamine at temperatures up to boiling temperature of the solvent in 5-24 hours.

The production of anilides according to process c) can, for example, be performed according to the methods described in DPS-3150918, by the ester of formula V being reacted with the corresponding aniline in the presence of trimethylaluminum, dimethylaluminum chloride or aluminum chloride in inert solvents such as toluene, benzene, hexane or methylene chloride optionally with cooling.

The introduction of the substituents in 6-position according to process d) can be performed, for example, according to A. Cerny et al. Coll. Czech. Chem. Comm. 49, 2828 (1984) or according to the process described in EP-21206, by the 6H compound of formula VII being reacted with the corresponding $R^6$ halides (bromides, chlorides, iodides). The reaction suitably takes place in an inert solvent such as dimethyl sulfoxide, dimethylformamide, acetonitrile or nitromethane in the presence of bases such as alkali hydroxides or alkali carbonates.

The introduction of substituent $R^2$ can take place, for example, according to the processes described in German patent application P 38 24 661.9. In this case, the Mannich base of formula VIII or its quaternary salt can be nucleophilically substituted or be introduced by the 2-aldehyde derivative as intermediate compound of desired substituent $R^2$. The nucleophilic exchange optionally takes place after quaternarization of the aminomethylene group in an inert solvent such as alcohols, polar, aprotic solvents, ethers or chlorinated hydrocarbons at room temperature or at a higher temperature, and alcoholates can be used as nucleophilic anions, which optionally can then be converted in the $CH_2$—OH-group. To produce the 2-methyl derivative, the compound of formula VIII can be reduced in polar solvents such as alcohols such as with sodium borohydride.

The oxidation to a 2-CHO compound can take place in inert solvents at room temperature analogously to the process with manganese dioxide or tert-butyl hypochlorite described in R. A. Jones et al. Synthetic Communications 16, 1799 (1986). The conversion of the 2-formyl compounds to compounds of formula I, in which $R^2$ means an alkenyl radical, can take place in a Wittig reaction, such as, for example, with alkyl triphenylphosphonium halide in polar solvents such as cyclic and acyclic ethers, chlorinated hydrocarbons, dimethylformamide or dimethyl sulfoxide, being performed at temperatures of $-50°$ C. up to the boiling temperature of the reaction mixture, and strong bases such as alkali alcoholates, lithium organyl, i.a., are added to generate ylene.

The preparation of substituents $R^2$ hydroxylated in 1-position can take place, for example, by a Grignardization or lithium alkylation of the 2-aldehydes or ketones. The Grignardization can take place with the usual Grignard reagents such as alkyl magnesium halides in an aprotic solvent such as cyclic and acyclic ethers at low temperatures ($-70°$ C. to $0°$ C.). The reaction with alkyl lithium takes place under analogous conditions.

The acetylation of a hydroxyl group can take place according to the usual methods such as, for example, by reaction with acid anhydrides or acid chlorides.

If substituent $R^2$ contains a hydroxyl group, the latter can, for example, be reduced by reaction with $NaBH_4$ in glacial acetic acid to the corresponding 2-alkyl derivative or be oxidized with manganese dioxide to the ketone or be dehydrated with introduction of a double bond. If substituent $R^2$ contains a double bond, the latter can, for example, be reduced catalytically. The introduction of substituent $R^2$—C(OH)R"R"' can take place, as described above, by Grignardization or lithium alkylation of the ketone.

To form salts, a compound of formula I is dissolved, for example, in a little methanol or methylene chloride and mixed with a concentrated solution of the desired acid.

The isomer mixtures can be separated into the diastereomers or E/Z isomers according to the usual methods such as, for example, crystallization, chromatography or the formation of salt.

The invention also includes compounds of the general formula IX

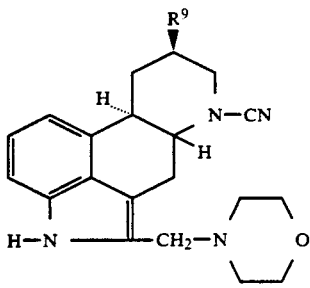

in which
R⁹ is CH₂OH or COOR, with R meaning $C_{1-4}$-alkyl; these compounds are valuable intermediate products for the production of pharmacologically effective compounds. The conversion of the intermediate products to the active substances takes place according to the above-described methods for introduction of the desired substituents in 8-, 6- or 2-position.

If the production of the initial compounds is not described, these compounds are known or are analogous to known compounds or producible analogously to processes described here.

The following examples are to explain the process according to the invention.

INITIAL MATERIAL

6-cyano-2-morpholinomethyl-8beta-ergoline-carboxylic acid methyl ester 3.54 g of 6-cyano-8beta-ergoline-carboxylic acid methyl ester (12 mmol), 9.46 g of morpholine hydrochloride (77 mmol) and 1.77 g of paraformaldehyde (59 mmol) are heated in 90 ml of dimethylformamide for 30 minutes at 100° C. After cooling, the mixture is poured on ice, made alkaline with sodium carbonate solution and shaken out five times with toluene. The organic phases are washed with water, dried with sodium sulfate and concentrated by evaporation. The precipitated crystals are suctioned off, yield 4.71 g (quantitative). The substance is chromatographed on silica gel with dichloromethane/methanol (98:1 and 9:1), 3.05 g (64% of theory) is isolated. The substance can be crystallized from dichloromethane/diisopropylether, the pure substance is obtained in 50% yield. $[\alpha]_D = +33.4°$ (0.5% in chloroform).

Preparation of 6-alkyl-2-morpholinomethyl-8beta-ergoline-carboxylic acid methyl ester 1) The desired Mannich base is obtained in a yield of 86% from 6-n-propyl-8beta-ergoline-carboxylic acid methyl ester according to the instructions above within a 2-hour reaction time.

2) 1.18 g of 6-cyano-2-morpholinomethyl-8beta-ergoline-carboxylic acid methyl ester (3 mmol) is dissolved in 180 ml of glacial acetic acid and 3 ml of water and reduced with 0.9 g of zinc dust in 5 hours at 110° C. The solvent is largely distilled off, the residue is dissolved in water and extracted with dichloromethane, yield of 0.04 g. The water phase is made alkaline with ammonia and sodium carbonate solution and again shaken out with dichloromethane, the basic fraction is 1.09 g of 2-morpholinomethyl-8beta-ergoline-carboxylic acid methyl ester, which is obtained pure by crystallization from diisopropylester, yield of 0.77 g (69% of theory), $[\alpha]_D = -40.3°$ C. (0.5% in chloroform). 185 mg of this substance (0.5 mmol) is dissolved in 10 ml of nitromethane and stirred together with 350 mg of potassium carbonate, 90 mg of tetrabutylammonium hydrogen sulfate and 0.24 ml of n-propyliodide (2.5 mmol) for 20 hours at 50° C. It is filtered off from the insolubles and the solution is concentrated by evaporation. The oily 2-morpholinomethyl-6-n-propyl-8beta-ergoline-carboxylic acid methyl ester is obtained in a yield of 70%.

Analogously, there is obtained:

6-cyclopropylmethyl-2-morpholinomethyl-8beta-ergoline-carboxylic acid methyl ester According to 1), the oily compound is obtained in a 73% yield according to chromatography.

6-allyl-2-morpholinomethyl-8beta-ergoline-carboxylic acid methyl ester

Prepared according to 2) in a 68% yield as oil.

6-ethyl-2-morpholinomethyl-8beta-ergoline-carboxylic acid methyl ester

Prepared according to 2) in a 71% yield as oil.

6-cyano-8beta-hydroxymethyl-2-morpholinomethyl-ergoline 3.95 g of 6-cyano-2-morpholinomethyl-8beta-ergoline-carboxylic acid methyl ester (10 mmol) is dissolved in 250 ml of tetrahydrofuran and 250 ml of methanol and altogether 4 g of sodium borohydride is added in four portions at room temperature. After two hours of reaction time, the organic phases are mixed with ice and common salt, shaken with ethyl acetate, combined and dried and concentrated by evaporation. After crystallization from the ethyl acetate, 3.26 g (89% of theory) is obtained, $[\alpha]_D = +46°$ (0.5% in pyridine).

Analogously, by reduction with sodium borohydride, the following alcohols are prepared:

8beta-hydroxymethyl-2-morpholinomethyl-6-n-propyl-ergoline from 2-morpholinomethyl-6-n-propyl-8beta-ergoline-carboxylic acid methyl ester, yield 40%, 6-ethyl-8beta-hydroxymethyl-2-morpholinomethyl-ergoline from 6-ethyl-2-morpholinomethyl-8beta-ergoline-carboxylic acid methyl ester, yield 73%, 6-allyl-8beta-hydroxymethyl-2-morpholinomethyl-ergoline from 6-allyl-2-morpholinomethyl-8beta-ergoline-carboxylic acid methyl ester, yield 65%, 6-cyclopropylmethyl-8beta-hydroxymethyl-2-morpholinomethyl-ergoline from 6-cyclopropylmethyl-2-morpholinomethyl-8beta-ergoline-carboxylic acid methyl ester, yield 73%, 6-alkyl-8beta-hydroxymethyl-2-morpholinomethyl-ergoline can be prepared by reduction and alkylation from 6-cyano-8beta-hydroxymethyl-2-morpholinomethyl-ergoline also according to above-described method 2).

8beta-hydroxymethyl-2-morpholinomethyl-6-n-propyl-ergoline Yield 40%, 6-cyclopropylmethyl-8beta-hydroxymethyl-2-morpholinomethyl-ergoline Yield 31%,

N-(6-cyano-8beta-methoxycarbonyl-2-ergolinyl-methyl)-N-methyl-morpholinium iodide 1.13 g of 6-cyano-2-morpholinomethyl-8beta-ergoline-carboxylic acid methyl ester is dissolved in 45 ml of tetrahydrofuran and stirred with 2.4 ml of methyl iodide at room temperature overnight. The crystalline precipitate is filtered off, yield 1.26 g (82% of theory), $[\alpha]_D = +9.7°$ (0.5% in DMSO).

N-(6-cyano-8beta-hydroxymethyl-2-ergolinyl-methyl)-N-methyl-morpholinium iodide The preparation takes place as described above from 6-cyano-8beta-hydroxymethyl-2-morpholinomethyl-ergoline in a yield of 81%.

6-cyano-2-methyl-8beta-ergoline-carboxylic acid methyl ester 107 mg of the above-prepared quaternary salt is dissolved in 5 ml of acetonitrile and reduced with 12 mg of sodium borohydride at room temperature in 45 minutes. It is acidified with 2N hydrochloric acid and, with addition of aqueous sodium bicarbonate solution, the substance is obtained as a crystalline precipitate, yield 47 mg (76% of theory), $[\alpha]_D = +40°$ (0.1% in chloroform).

6-cyano-8beta-hydroxymethyl-2-methyl-ergoline

The compound can be prepared by reduction of the above ester with sodium borohydride or by reduction of the quaternary salt of the ester (in methanol) or the 8beta-hydroxymethyl compound.

2-methyl-6-n-propyl-8beta-ergoline-carboxylic acid methyl ester

As described at the beginning, the noncrystalline compound can be prepared from 6-cyano-2-methyl-8beta-ergoline-carboxylic acid methyl ester by reduction and alkylation with n-propyliodide in a 54% yield.

6-allyl-2-methyl-8beta-ergoline-carboxylic acid methyl ester

The allyl compound is obtained by alkylation with allyl bromide in a 63% yield.

6-cyclopropylmethyl-2-methyl-8beta-ergoline-carboxylic acid methyl ester

The cyclopropylmethyl compound is obtained by alkylation with cyclopropylmethyl chloride and lithium iodide in a 43% yield.

6-ethyl-2-methyl-8beta-ergoline carboxylic acid methyl ester

The 6-ethyl compound is obtained by alkylation with ethyl iodide in a 46% yield.

The 6-alkyl-8beta-hydroxymethyl-2-methyl-ergoline can take place as described in the beginning by reduction of the above-described ester with sodium borohydride in methanol or by reduction and alkylation of the 6-cyano-8beta-hydroxymethyl-2-methyl-ergoline.

6-cyclopropylmethyl-8beta-hydroxymethyl-2-methyl-ergoline

Yield 57%.

8beta-hydroxymethyl-2-methyl-6-n-propyl-ergoline

Yield 69%

8beta-hydroxymethyl-2-methoxymethyl-6-n-propyl-ergoline 1 g of sodium is dissolved under inert gas in 100 ml of methanol. To it is added 2.8 g of N-(6-cyano-8beta-hydroxymethyl-2-ergolinyl-methyl)-N-methylmorpholinium iodide and stirred for 1.5 hours at room temperature. The clear solution is concentrated by evaporation and poured into a half-saturated common salt solution with cooling. The crystals are suctioned off, yield 1.59 g. The crude product is heated in 40 ml of a 30% solution of potassium hydroxide in water/ethanol 1:1 for 5 hours to 100° C., poured after cooling into a half-saturated common salt solution and shaken with n-butanol. The solvent is completely evaporated and the residue of 1.56 g is taken up in 100 ml of nitromethane. This solution is mixed with 3 g of potassium carbonate, 0.78 g of tetrabutylammonium hydrogen sulfate and 2.7 ml of n-propyliodide and stirred for 16 hours at 50° C. After cooling, it is filtered off from the precipitate, the filtrate is concentrated by evaporation and the residue is chromatographed on silica gel with ethyl acetate/methanol (8:2), yield 1.4 g (86% of theory), $[\alpha]_D = -78°$ (0.1% in chloroform).

6-ethyl-8beta-hydroxymethyl-2-methoxymethyl-ergoline

By using ethyliodide instead of n-propyliodide, the compound is obtained in a 72% yield.

6-allyl-8beta-hydroxymethyl-2-methyoxymethyl-ergoline

By using allylbromide instead of n-propyliodid, the compound is obtained in a 63% yield.

8beta-hydroxymethyl-2-methylthiomethyl-6-n-propyl-ergoline

The quaternary salt is dissolved in dichloromethane and reacted with the 10-times excess of sodium methanethiolate at room temperature in 4 hours. After hydrolysis of the nitrile and alkylation, the desired alcohol is obtained in a yield of 63%.

6-cyano-8beta-methoxycarbonyl-2-ergoline-carbaldehyde 7.89 g of 6-cyano-2-morpholinomethyl-8beta-ergoline-carboxylic acid methyl ester (20 mmol) is dissolved in 400 ml of anhydrous tetrahydrofuran, the solution is cooled to −40° C., mixed with 4 ml of triethylamine and then the solution of 3.0 ml of tert-butyl hypochloride (25 mmol) in 60 ml of anhydrous tetrahydrofuran is instilled. After 10 minutes of stirring, another 1 ml of tert-butylhypochlorite is added, stirred for 5 minutes and the solution is poured on ice. The mixture is made alkaline with bicarbonate solution and shaken with ethyl acetate. The organic phases are dried, the solvent is evaporated and the residue is crystallized from the diisopropylether, the yield is quantitative $[\alpha]_D = +42.7°$ (0.5% in chloroform).

6-cyano-8beta-hydroxymethyl-2-ergoline-carbaldehyde

Is prepared from 6-cyano-8beta-hydroxymethyl-2-morpholinomethyl-ergoline in the same way in an 87% yield.

6-cyano-2-hydroxymethyl-8beta-ergoline-carboxylic acid methyl ester 161 mg of 6-cyano-8beta-methoxycarbonyl-2-ergoline-carbaldehyde (5 mmol) is dissolved in 10 ml of acetonitrile and reduced with 30 ml of sodium borohydride at room temperature in 1 hour. The solvent is largely evaporated, acidified with 2N hydrochloric acid and with addition of aqueous sodium bicarbonate solution the substance is obtained, yield 83%.

6-cyclopropylmethyl-2-formyl-8beta-ergoline-carboxylic acid methyl ester

As described above, the aldehyde is prepared from the 6-cyclopropylmethyl-2-morpholinomethyl-8beta-ergoline-carboxylic acid methyl ester by oxidation with tert-butylhypochlorite. All the ergoline-aldehydes alkylated in 6-position are used as crude products in the Wittig reaction.

6-n-propyl-2-formyl-8beta-ergoline-carboxylic acid methyl ester

The aldehyde is obtained from the corresponding Mannich base by oxidation with trichloroisocyanuric acid in dichloromethane and triethylamine at −78° C. in approximately 80% yield.

6-ethyl-2-formyl-8beta-ergoline-carboxylic acid methyl ester Prepared as above from the corresponding Mannich base, yield 49%.

6-allyl-2-formyl-8beta-ergoline-carboxylic acid methyl ester

Prepared as above from the corresponding Mannich base, yield 65%.

6-alkyl-8beta-hydroxymethyl-2-ergoline-carbaldehyde

The aldehydes are obtained from the corresponding Mannich bases by oxidation with trichloroisocyanuric acid in a 35 to 76% yield.

6-n-propyl-2-vinyl-8beta-ergoline-carboxylic acid methyl ester 10.0 g of methyltriphenylphosphonium bromide (28 mmol) is suspended in 100 ml of anhydrous tetrahydrofuran, cooled to −70° C. and 3.45 g of potassium-tert-butylate is added. After 15 minutes of stirring, the solution of 1.9 g of crude 6-n-propyl-2-formyl-8beta-ergoline-carboxylic acid methyl ester (about 5.6 mmol), dissolved in 5 mmol of anhydrous tetrahydrofuran is instilled and the mixture is allowed to warm to −20° C. in three hours. Then, it is mixed with saturated common salt solution and extracted with ethyl acetate. The organic phase is dried and concentrated by evaporation, the residue is chromatographed on silica gel with hexane/acetone 7:3, and 0.94 g is isolated (yield 40% relative to Mannich base), $[\alpha]_D = -100°$ (0.5% in chloroform).

Analogously, there are prepared:

6-cyclopropylmethyl-2-vinyl-8beta-ergoline-carboxylic acid methyl ester

The Wittig reaction with the corresponding aldehyde yields the product in a 43% yield (relative to the Mannich base), $[\alpha]_D = -140°$ (0.1% in chloroform).

6-allyl-2-vinyl-8beta-ergoline-carboxylic acid methyl ester

The Wittig reaction with the corresponding aldehyde yields the product in a 33% yield.

6-ethyl-2-vinyl-8beta-ergoline-carboxylic acid methyl ester

The Wittig reaction with the corresponding aldehyde yields the product in a 41% yield.

6-alkyl-8beta-hydroxymethyl-2-vinyl-ergoline

The 2-vinyl compounds can be obtained as described in the beginning by reduction of the esters with sodium borohydride or lithium aluminum hydride or by a Wittig reaction with the corresponding 6-alkyl-8beta-hydroxymethyl-2-ergoline-carbaldehyde.

8beta-hydroxymethyl-6-n-propyl-2-vinyl-ergoline

Yield 89%, $[\alpha]_D = -113°$ (0.5% in DMSO).

6-ethyl-8beta-hydroxymethyl-2-vinyl-ergoline

Yield 73%, $[\alpha]_D = -82°$ (0.5% in chloroform).

6-allyl-8beta-hydroxymethyl-2-vinyl-ergoline

Yield 56%.

6-cyclopropylmethyl-8beta-hydroxymethyl-2-vinyl-ergoline

Yield 64%.

2-ethyl-6-n-propyl-8beta-ergoline-carboxylic acid methyl ester 0.83 g of 6-n-propyl-2-vinyl-8beta-ergoline-carboxylic acid methyl ester (2.5 mmol) is dissolved in 50 ml of methanol, mixed with 80 g of palladium/carbon 10% and hydrogenated at standard pressure and room temperature. After 10 minutes, the absorption is completed, it is filtered off and the filtrate is concentrated by evaporation. The residue is crystallized, yield of 800 mg (94% of theory) $[\alpha]_D = -63°$ (0.1% in chloroform).

6-cyclopropylmethyl-2-ethyl-8beta-ergoline-carboxylic acid methyl ester

Is obtained from the 2-vinyl compound by hydrogenation in quantitative yield.

2-6-diethyl-8beta-ergoline-carboxylic acid methyl ester

Is obtained from the 2-vinyl compound by hydrogenation and crystallization from ethyl acetate/hexane in an 87% yield.

6-alkyl-2-hydroxymethyl-8beta-ergoline-carboxylic acid methyl ester

Can be prepared as described in the beginning, by reduction of the 2-aldehydes with sodium borohydride in acetonitrile or by reduction of the 6-cyano-2-hydroxymethyl-carboxylic acid methyl ester with zinc in glacial acetic acid and subsequent alkylation.

2-hydroxymethyl-6n-propyl-8beta-ergoline-carboxylic acid methyl ester

Yield 73%.

6-ethyl-2-hydroxymethyl-8beta-ergoline-carboxylic acid methyl ester

Yield 77%.

6-cyclopropylmethyl-2-hydroxymethyl-8beta-ergoline-carboxylic acid methyl ester

Yield 62%.

6-allyl-2-hydroxymethyl-8beta-ergoline-carboxylic acid methyl ester

Yield 51%.

2-hydroxyethyl-8beta-hydroxymethyl-6-n-propyl-ergoline 998 mg of 8beta-hydroxymethyl-6-n-propyl-2-ergoline-carbaldehyde (3.2 mmol) is dissolved in 100 ml of anhydrous tetrahydrofuran, cooled to −65° C. and mixed with 20 mmol of a solution of methylmagnesium bromide in ether (10 mmol of methyllithium in ether). After the addition, it is allowed to thaw, stirred for another 30 minutes at room temperature and poured on ice. The organic phases are extracted with ethyl acetate, dried and concentrated by evaporation. The substance precipitates as isomer mixture which can be separated chromatographically.

2-(1-hydroxypropyl)-8beta-hydroxymethyl-6-n-propyl-ergoline

Can be prepared analogously with ethylmagnesium bromide.

2-acetyl-8beta-hydroxymethyl-6-n-propyl-ergoline 328 mg of 2-hydroxyethyl-8beta-hydroxymethyl-6-n-propyl-ergoline (1 mmol) is dissolved in 20 ml of dichloromethane, 865 mg of manganese dioxide (active, 10 mmol) is added and stirred overnight at room temperature. Then, it is filtered on aluminum oxide and the pure product isolated after chromatography, yield 212 mg (65% of theory).

8beta-acetoxymethyl-2-(1-hydroxy-1-methyl-ethyl)-6-n-propyl-ergoline

The above compound is acetylated in pyridine with acetic anhydride. The crude product is reacted, as described above, with methyllithium, and 143 mg of product (68% of yield) is obtained from 200 mg of 2-acetyl-8beta-hydroxymethyl-6-n-propyl-ergoline after chromatography.

8beta-acetoxymethyl-2-isopropenyl-6-n-propyl-ergoline 115 mg of tertiary alcohol (0.3 mmol) is dissolved in 15 ml of tetrahydrofuran and 0.5 ml of triethylamine and stirred with 0.3 ml of methanesulfonic acid chloride for 30 minutes at room temperature. Then, the mixture is poured on ice, made alkaline with ammonia and extracted with ethyl acetate. After drying and evaporation of the solvent, the residue is chromatographed, yield 85 mg (69% of theory).

8beta-acetoxymethyl-2-isopropyl-6-n-propyl-ergoline

The above compound is hydrogenated as described above in methanol with palladium/carbon at 10% in normal pressure and room temperature. The yield is quantitative.

EXAMPLE 1

2-methyl-8beta-methylthiomethyl-6-n-propyl-ergoline 345 mg of 2-methyl-6-n-propyl-8beta-ergoline-carboxylic acid methyl ester (1.06 mmol) is dissolved in 10 ml of anhydrous dioxane and heated with 150 mg of lithium aluminum hydride for 90 minutes to 80° C. After the cooling, 0.15 ml of water, 0.15 ml of 15% sodium hydroxide solution and 0.45 ml of water are added in succession, the precipitate is filtered off and the filtrate is concentrated by evaporation, quantitative yield. The crude alcohol is dissolved in 5 ml of pyridine and stirred with 0.25 ml of methanesulfonyl chloride for one hour at room temperature. Ice is added, it is stirred for another 30 minutes, and it is made alkaline with ammonia. The mixture is extracted with dichloromethane, the organic phase is dried and concentrated by evaporation. The residue of 388 mg is dissolved in 5 ml of N,N-dimethylacetamide and 720 mg of sodium methyl mercaptide (10 mmol) is stirred for an hour at room temperature. Ice is added to the mixture and it is extracted with dichloromethane. The organic phases are dried and concentrated by evaporation. 175 mg is crystallized from methanol, yield 50% $[\alpha]_D = -80°$ (0.5% in chloroform).

EXAMPLE 2

Analogously to example 1, 6-ethyl-2-methyl-8beta-methylthiomethylergoline is produced from 6-ethyl-2-methyl-8beta-ergoline-carboxylic acid methyl ester in a 38% yield.

6-allyl-2-methyl-8beta-methylthiomethyl-ergoline is produced from 6-allyl-2-methyl-8beta-ergoline-carboxylic acid methyl ester in a 58% yield.

6-cyclopropylmethyl-2-methyl-8beta-methylthiomethyl-ergoline is produced from 6-cyclopropylmethyl-2-methyl-8beta-ergoline-carboxylic acid methyl ester in a 32% yield, $[\alpha]_D = -97°$ (0.5% in chloroform).

2-ethyl-6-n-propyl-8beta-methylthiomethyl-ergoline is produced from 2-ethyl-6-n-propyl-8beta-ergoline-carboxylic acid methyl ester in an 81% yield $[\alpha]_D = -78°$ (0.5% in chloroform)

6-cyclopropylmethyl-2-ethyl-8beta-methylthiomethyl-ergoline is produced from 6-cyclopropyl-methyl-2-ethyl-8beta-ergoline-carboxylic acid methyl ester in a 43% yield, $[\alpha]_D = -100°$ (0.5% in chloroform).

8beta-methylthiomethyl-6-n-propyl-2-vinyl-ergoline is produced from 6-n-propyl-2-vinyl-8beta-ergoline-carboxylic acid methyl ester in a 29% yield, $[\alpha]_D = -106°$ (0.1% in chloroform).

6-allyl-8beta-methylthiomethyl-2-vinyl-ergoline is produced from 6-allyl-2-vinyl-8beta-ergoline-carboxylic acid methyl ester in a 37% yield.

6-cyclopropylmethyl-8beta-methylthiomethyl-2-vinyl-ergoline is produced from 6-cyclopropyl-methyl-2-vinyl-8beta-ergoline-carboxylic acid methyl ester in a 34% yield, $[\alpha]_D = -131°$ (0.1% in chloroform).

8beta-methoxymethyl-2-methyl-6-n-propyl-ergoline is produced from 2-methyl-6-n-propyl-8beta-ergoline-carboxylic acid methyl ester by nucleophilic displacement of the mesyl group with sodium methylate, yield 20%, $[\alpha]_D = -72°$ (0.1% in chloroform).

2-methoxymethyl-8beta-methylthiomethyl-6-n-propyl-ergoline is produced from 8beta-hydroxymethyl-2-methoxymethyl-6-n-propyl-ergoline as tartrate in a 73% yield, $[\alpha]_D = -46°$ (0.5% in pyridine).

6-ethyl-2-methoxymethyl-8beta-methylthiomethyl-ergoline is produced from 6-ethyl-8beta-hydroxy-methyl-2-methoxymethylergoline in a 27% yield.

2,8beta-bis-(methylthiomethyl)-6-n-propyl-ergoline is produced from 8beta-hydroxymethyl-2-methylthiomethyl-6-propyl-ergoline in a 42% yield. 2-acetoxymethyl-8beta-methylthiomethyl-6-n-propyl-ergoline is produced from 2-hydroxymethyl-6-n-propyl-8beta-ergoline-carboxylic acid methyl ester by acetylation (pyridine, acetic anhydride) and as described in example 1, conversion in position 8 in a 28% yield.

2-hydroxymethyl-8beta-methylthiomethyl-6-n-propyl-ergoline is produced from the above preparation by saponification with methanolic KOH at room temperature, yield 86%. 2-isopropenyl-8beta-methylthiomethyl-6-n-propyl-ergoline is produced from 8beta-acetoxymethyl-2-isopropenyl-6-n-propyl-ergoline by saponification with methanolic KOH and then conversion in position 8 in a 47% yield.

EXAMPLE 3

(2-methyl-6-n-propyl-8beta-ergolinyl)-acetonitrile 8-hydroxymethyl-2-methyl-6-n-propyl-ergoline is converted to the mesylate/$[\alpha]_D = -62.9°$ (0.5% in chloroform) as described in example 1. 4.9 g of 8beta-mesyloxymethyl-2-methyl-6-n-propyl-ergoline (813 mmol) is heated in 300 ml of dimethylformamide with 19.6 g of potassium cyanide for 16 hours at 80° C. The mixture is added to ice water and crystals are filtered off after 30 minutes of stirring, yield 3.8 g (96% of theory), $[\alpha]_D = -90°$ (0.5% in chloroform).

From the corresponding mesylates, there were produced:
(2-ethyl-6-n-propyl-8beta-ergolinyl)-acetonitrile, yield 92%, $[\alpha]_D = -84°$ (0.5% in chloroform)
(6-n-propyl-2-vinyl-8beta-ergolinyl)-acetonitrile, yield 96%, $[\alpha]_D = -117°$ (0.5% in chloroform)
(6-ethyl-2-vinyl-8beta-ergolinyl)-acetonitrile, yield 73%
(6-allyl-2-vinyl-8beta-ergolinyl)-acetonitrile, yield 65%
(2-methoxymethyl-6-n-propyl-8beta-ergolinyl)-acetonitrile, yield 91%, $[\alpha]_D = -91°$ (0.5% in chloroform).

EXAMPLE 4

(2-methyl-6-n-propyl-8beta-ergolinyl)-acetamide 922 mg of (2-methyl-6-n-propyl-8beta-ergolinyl)-acetonitrile (3 mmol) is dissolved in 15 ml of a 30% solution of HBr in glacial acetic acid and stirred for 3 hours at room temperature. The mixture is mixed with ice, made alkaline with ammonia and shaken with ethyl acetate. The organic phases are dried and concentrated by evaporation. The residue is chromatographed on silica gel with acetone/methanol and crystallized from ethyl acetate, yield 421 mg (43% of theory), $[\alpha]_D = -67°$ (0.5% in pyridine).

EXAMPLE 5

From the corresponding nitriles, the following acetamides are prepared by hydrolysis analogously to example 4:
(2-ethyl-6-n-propyl-8beta-ergolinyl)-acetamide, yield 42%, $[\alpha]_D: = -58°$ (0.5% in pyridine)
(6-n-propyl-2-vinyl-8beta-ergolinyl)-acetamide, yield 18%, $[\alpha]_D: = -54°$ (0.5% in pyridine)
(6-ethyl-2-vinyl-8beta-ergolinyl)-acetamide, yield 49%
(6-allyl-2-vinyl-8beta-ergolinyl)-acetamide, yield 37%
(2-methoxymethyl-6-n-propyl-8beta-ergolinyl)-acetamide, yield 14%, $[\alpha]_D = -42°$ (0.1% in pyridine).

EXAMPLE 6

3-ethyl-1-(3-dimethylaminopropyl)-1-(6-n-propyl-2-vinyl-8beta-ergolinylcarbonyl)-urea 0.81 g of 6-n-propyl-2-vinyl-8beta-ergoline-carboxylic acid methyl ester (2.4 mmol) is dissolved in 5 ml of dioxane, mixed with 1.2 ml of 14N-KOH and heated for 2 hours to 80° C. After the cooling, it is diluted with 10 ml of water, neutralized with phosphoric acid and sodium dihydrogen phosphate solution to pH 6.5–7 and extracted with n-butanol. The organic phase is carefully evaporated to dryness, suspended in 100 ml of tetrahydrofuran and mixed with 0.77 ml of triethylamine and 0.90 g of N-(3-dimethylaminopropyl)-N'-ethylcarbodiimide, hydrochloride (4.7 mol). The mixture is refluxed for 16 hours, mixed with bicarbonate solution after the cooling and shaken out with ethyl acetate. The organic phase is dried and concentrated by evaporation, the residue is chromatographed on silica gel with hexane/acetone. The substance is isolated as tartrate, yield 775 mg (42% of theory), $[\alpha]_D = -39°$ (0.5% in pyridine).

From the above-described esters, the following ureas are prepared analogously to example 5:
3-ethyl-1-(3-dimethylaminopropyl)-1-(2-methyl-6-n-propyl-8beta-ergolinylcarbonyl)-urea, yield 28%, as tartrate, $[\alpha]_D = -28°$ (0.5% in pyridine).
3-ethyl-1-(3-dimethylaminopropyl)-1-(2-ethyl-6-n-propyl-8beta-ergolinyl-carbonyl)-urea, yield 36% as tartrate, $[\alpha]_D = -37°$ (0.5% in pyridine).
1-(6-allyl-2-methyl-8beta-ergolinylcarbonyl)-3-ethyl-1-(3-dimethylaminopropyl)-urea, yield 41% as tartrate.
1-(6-allyl-2-vinyl-8beta-ergolinylcarbonyl)-3-ethyl-1-(3-dimethylaminopropyl)-urea, yield 27% as tartrate.
1-(2,6-diethyl-8beta-ergolinylcarbonyl)-3-ethyl-1-(3-dimethylaminopropyl)-urea, yield 33% as a tartrate.
1-(6-cyclopropylmethyl-2-methyl-8beta-ergolinylcarbonyl)-1-(3-dimethylaminopropyl)-3-ethyl-urea, yield 19% as a tartrate, $[\alpha]_D = -38°$ (0.5% in pyridine).
1-(6-cyclopropylmethyl-2-ethyl-8beta-ergolinylcarbonyl)-3-ethyl-1-(3-dimethyl-aminopropyl)-urea, yield 22% as tartrate, $[\alpha]_D = -45°$ (0.5% in pyridine).
1-(6-cyclopropylmethyl-2-vinyl-8beta-ergolinylcarbonyl)-3-ethyl-1-(3-dimethyl-aminopropyl)-urea, yield 28% as tartrate, $[\alpha]_D = -42°$ (0.5% in pyridine).
1-(3-dimethylaminopropyl)-3-ethyl-1-(2-methoxymethyl-6-n-propyl-8-ergolinyl-carbonyl)-urea, yield 29%.

EXAMPLE 7

2-methyl-6-n-propyl-8beta-ergoline-carboxylic acid-(4-methoxyanilide)

985 mg of 4-anisidine (8 mmol), dissolved in 8 ml of toluene, is instilled in the solution of 6.8 mmol of toluene, is instilled in the solution of 6.8 mmol of trimethylaluminum in 5 ml of toluene with cooling to 0° C. After 30 minutes of stirring at room temperature, the solution of 652 mg of 2-methyl-6-n-propyl-8beta-ergoline-carboxylic acid methyl ester (2 mmol) in 6 ml of toluene is added with ice cooling at room temperature and is stirred for 1 hour. 5 ml of water and 1.5 g of tartaric acid are carefully added at room temperature, acidified with 1 N hydrochloric acid and stirred for 15 minutes at room temperature. Then, it is made alkaline with ammonia, extracted with ethyl acetate, the organic phases are dried and concentrated by evaporation. The residue is chromatographed on silica gel with dichloromethane/methanol and crystallized from ethyl acetate, yield 44%, $[\alpha]_D = -64°$ (0.5% in chloroform).

EXAMPLE 8

6-n-propyl-2-vinyl-8beta-ergoline-carboxylic acid-(4-fluoroanilide)

The relevant ester is reacted as described in example 7, except dimethylaluminum chloride is used here instead of trimethylaluminum.

Yield 51%, $[\alpha]_D = -70°$ (0.5% in chloroform).

6-n-propyl-2-vinyl-8beta-ergoline-carboxylic acid-(3-fluoroanilide)

Yield 43%.

6-n-propyl-2-vinyl-8beta-ergoline-carboxylic acid-(4-methoxyanilide)

Yield 61%.

2-methoxymethyl-6-n-propyl-8beta-ergoline-carboxylic acid-(4-methoxyanilide)

Yield 74%.

EXAMPLE 9

Additional anilides were prepared according to the following instructions:

1 mmol of ester is dissolved in 10 ml of dichloromethane, 4 mmol of aniline and 4 mmol of aluminum chloride are added and stirred for 3 hours at room temperature. Then, ice and, after 30 minutes, tartaric acid are added, it is made alkaline with concentrated ammonia and extracted with dichloromethane. The organic phases are dried and concentrated by evaporation, the residue is chromatographed on silica gel with hexane/acetone.

2-methyl-6-n-propyl-8beta-ergoline-carboxylic acid-(4-fluoroanilide)

Yield 58%, $[\alpha]_D = -59°$ (0.1% in chloroform)

2-methyl-6-n-propyl-8beta-ergoline-carboxylic acid-(3-fluoroanilide)

Yield 28%, $[\alpha]_D = -53°$ (0.1% in chloroform)

6-allyl-2-ethyl-8beta-ergoline-carboxylic acid-(4-fluoroanilide)

Yield 61%.

6-cyclopropylmethyl-2-methyl-8beta-ergoline-carboxylic acid-(4-fluoroanilide)

Yield 81%.

We claim:
1. A compound of formula I

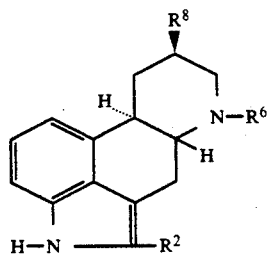

wherein
$R^2$ is $C_{1-7}$ alkyl, $C_{2-7}$ alkenyl, $CH_2-O-C_{1-4}$ alkyl or $CH_2-S-C_{1-4}$ alkyl, optionally substituted by a hydroxy, $C_{1-4}$-alkoxy, or $C_{2-5}$-carboxylic acid acyloxy group;

$R^6$ is $C_{2-6}$ alkyl, $C_{3-6}$ alkenyl or $C_{3-5}$-cycloalkyl-$C_{1-2}$ alkyl and
$R^8$ is $CH_2-X$ or

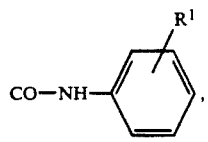

wherein
X is CN, $OCH_3$, $SCH_3$ or $CONH_2$,
$R^1$ is hydrogen, halogen, methyl or methoxy, and
$R^3$ is $C_{1-4}$ alkyl or $(CH_2)_n-N(CH_3)_2$, wherein n=1–4,
or an acid addition salt thereof.

2. A compound of formula IX

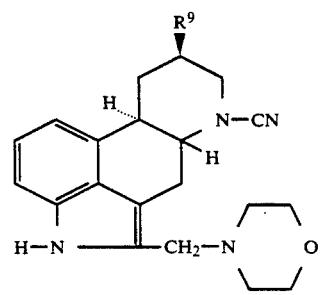

wherein
$R^9$ is $CH_2OH$ or $COOR$, wherein R is a $C_{1-4}$ alkyl group.

3. 2-methyl-8β-methylthiomethyl-6-n-propyl-ergoline, 6-ethyl-2-methyl-8β-methylthiomethyl-ergoline, 6-allyl-2-methyl-8β-methylthiomethyl-ergoline, 6-cyclopropylmethyl-2-methyl-8β-methylthiomethyl-ergoline, 2-ethyl-6-n-propyl-8β-methylthiomethyl-ergoline, 6-cyclopropylmethyl-2-ethyl-8β-methylthiomethyl-ergoline, 8β-methylthiomethyl-6-n-propyl-2-vinyl-ergoline, 6-allyl-8β-methylthiomethyl-2-vinyl-ergoline, 6-cyclopropylmethyl-8β-methylthiomethyl-2-vinyl-ergoline, 2-methoxymethyl-8β-methylthiomethyl-6-n-propyl-ergoline, 6-ethyl-2-methoxymethyl-8β-methylthiomethyl-ergoline, 2,8β-bis-methylthiomethyl-6-n-propyl-ergoline, 2-acetoxymethyl-8β-methylthiomethyl-6-n-propyl-ergoline, 2-hydroxymethyl-8β-methylthiomethyl-6-n-propyl-ergoline, 2-isopropenyl-8β-methylthiomethyl-6-n-propyl-ergoline, (2-methyl-6-n-propyl-8β-ergolinyl)-acetonitrile, (2-ethyl-6-n-propyl-8β-ergolinyl)-acetonitrile, (6-n-propyl-2-vinyl-8β-ergolinyl)-acetonitrile, (2-methoxymethyl-6-n-propyl-8β-ergolinyl)-acetonitrile, (6-ethyl-2-vinyl-8β-ergolinyl)-acetonitrile, (6-allyl-2-vinyl-8β-ergolinyl)-acetonitrile, (2-methyl-6-n-propyl-8β-ergolinyl)-acetamide, (2-ethyl-6-n-propyl-8β-ergolinyl)-acetamide, (6-n-propyl-2-vinyl-8β-ergolinyl)-acetamide, (6-ethyl-2-vinyl-8β-ergolinyl)-acetamide, (6-allyl-2-vinyl-8β-ergolinyl)-acetamide, 2-methyl-6-n-propyl-8β-ergoline-carboxylic acid-(4-fluoroanilide),
6-n-propyl-2-vinyl-8β-ergoline-carboxylic acid-(4-fluoroanilide),
2-methyl-6-n-propyl-8β-ergoline-carboxylic acid-(4-methoxyanilide),
2-methyl-6-n-propyl-8β-ergoline-carboxylic acid-(3-fluoroanilide), 6-allyl-2-ethyl-8β-ergoline-carboxylic acid-(4-fluoroanilide),
6-cyclopropylmethyl-2-methyl-8β-ergoline-carboxylic acid-(4-fluoroanilide), or
2-methoxymethyl-6-n-propyl-8β-ergoline-carboxylic acid-(4-methoxyanilide), each a compound of claim 1.

4. A pharmaceutical preparation comprising an effective amount of a compound of claim 1 and a pharmaceutically acceptable excipient.

5. A pharmaceutical preparation comprising an effective amount of a compound of claim 3 and a pharmaceutically acceptable excipient.

* * * * *